United States Patent
Hartmann

[11] Patent Number: 6,113,791
[45] Date of Patent: Sep. 5, 2000

[54] PROCESS FOR FLUSHING THE FILTRATION MODULES OF A UNIT FOR CLARIFYING LIQUIDS

[75] Inventor: Eduard Hartmann, Schneisingen, Switzerland

[73] Assignee: Bucher-Guyer AG, Niederweningen, Switzerland

[21] Appl. No.: 07/836,267

[22] PCT Filed: Jun. 21, 1991

[86] PCT No.: PCT/CH91/00134

§ 371 Date: Mar. 3, 1992

§ 102(e) Date: Mar. 3, 1992

[87] PCT Pub. No.: WO92/00797

PCT Pub. Date: Jan. 23, 1992

[30] Foreign Application Priority Data

Jul. 6, 1990 [CH] Switzerland .................. 2270/90-2

[51] Int. Cl.[7] .................................. B01D 65/06
[52] U.S. Cl. .......................... 210/636; 210/797
[58] Field of Search .................. 210/321.69, 636, 210/791, 797

[56] References Cited

U.S. PATENT DOCUMENTS 3,956,114  5/1976  Del Pico et al. ............. 210/636

FOREIGN PATENT DOCUMENTS

| 321751 | 6/1989 | European Pat. Off. . |
| 3818437 | 12/1989 | Germany . |
| 116281 | 10/1978 | Japan ............................ 210/636 |
| WO 8903240 | 4/1986 | WIPO ............................ 210/636 |
| 88/00494 | 1/1988 | WIPO . |

OTHER PUBLICATIONS

Faust et al., "Einsatz von Cross–flow–Techniken in der Bioverfahrenstechnik," Jun. 1989, pp. 459–468.

*Primary Examiner*—Matthew O. Savage
*Attorney, Agent, or Firm*—Burns, Doane, Swecker & Mathis

[57] ABSTRACT

The process for flushing filtration modules of a cross flow filtration device is carried out in a unit that is used for the clarification of liquids in a retentate circulation circuit. When the unit is shut down, for example as the result of a power failure, filtration modules are flushed free of solid particles by the supply of an addition of flushing agent that increases over time and/or geometrically into the retentate side of the cross flow filtration device. As a result, the danger of clogging of the filtration modules is largely avoided.

21 Claims, 1 Drawing Sheet

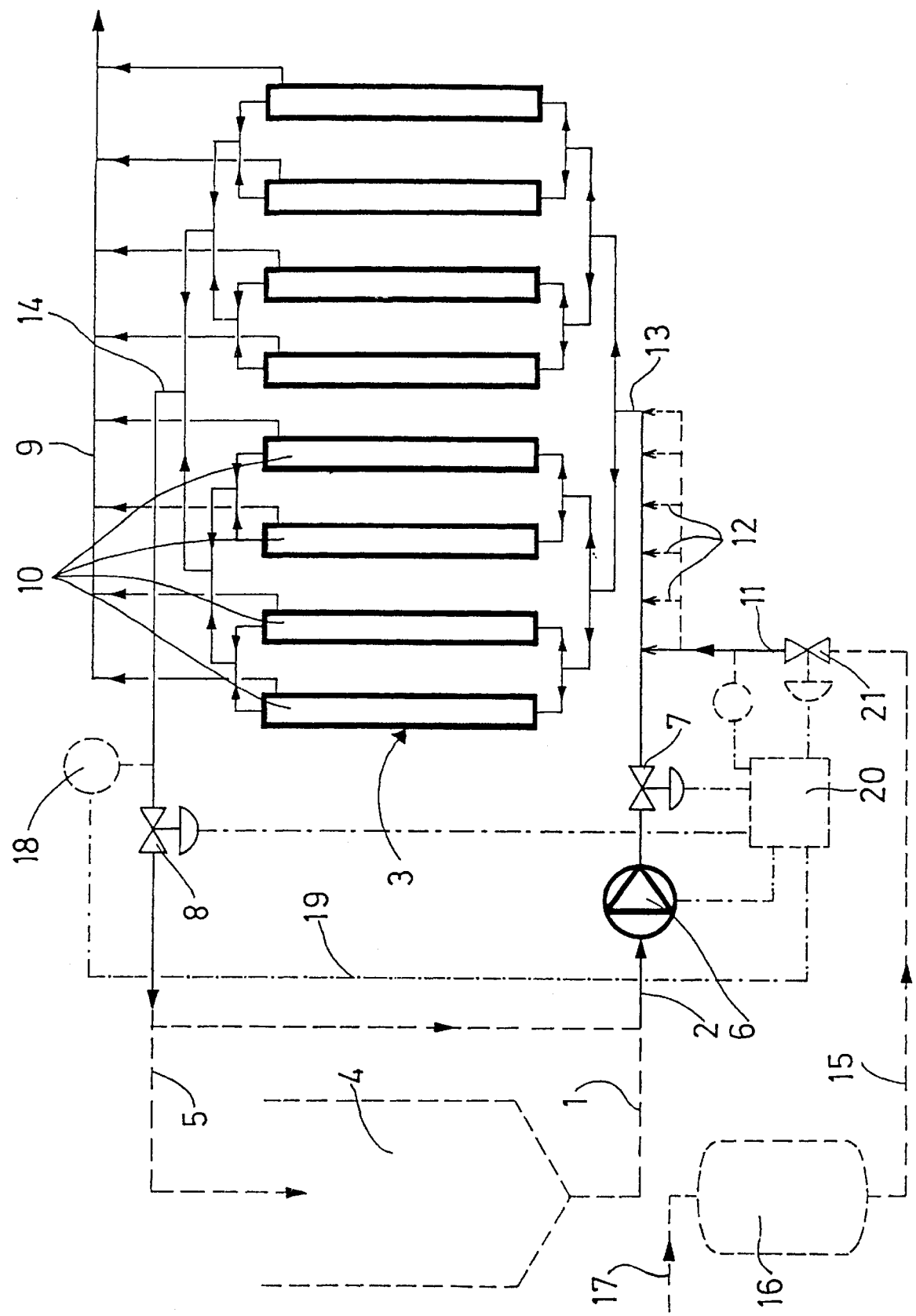

PROCESS FOR FLUSHING THE FILTRATION MODULES OF A UNIT FOR CLARIFYING LIQUIDS

FIELD OF THE INVENTION

The invention relates to a process for flushing filtration modules of a unit for clarifying liquids, in particular raw juice from vegetable products or biotechnologically manufactured products by cross flow filtration, in particular microfiltration or ultrafiltration, which is run with a high proportion of solids in the retentate circulation cycle.

BACKGROUND OF THE INVENTION

The raw juice extracted from vegetable products can be both alcoholic and non-alcoholic raw juices, for example raw juice from fruit, grapes, berries or other fruits and vegetables, as well as oil seeds for extracting oil. Also products derived from several vegetable products, for example beers in particular in connection with beer recovery from fermenter or tank storage yeast, are suitable.

Through WO 89/02708 it is known, how to proceed in the clarification of liquids with a high proportion of solids in the retentate circulation cycle. Thus the objective is pursued to improve the filtration yield of the diaphragms significantly.

Because of the high proportion of solids in the retentate circulation cycle, the danger exists in such units that the filtration modules of the cross flow filtration device become clogged. Particularly when the unit is suddenly shut down, as for example when there is a power failure, or an interruption of control air for the pneumatically operated devices etc., all retentate conduits of the cross flow filtration system must be flushed out as quickly as possible. If this does not take place immediately, the viscosity of the retentate increases, because the retentate is athixotropic liquid and the liquid is no longer being moved when the retentate circulating pump stops. As a consequence the filtration modules possibly can no longer be flushed out with flushing agents or have to be cleaned out conduit by conduit at great expense mechanically, but most often by hand. Generally, this is only possible in modules with wide conduits, narrow conduits become clogged irreversibly.

This problem is even further complicated in that an operation often has to be performed at a higher than average proportion of cloudiness in the retentate cycle to operate the cross flow filtration with drastically increased filtration yield.

To avoid these drawbacks, it is known, when the unit shuts down, to feed water to the retentate cycle to flush the modules. The delivery of water takes place upstream from the circulating pump for the retentate and is carried out in a known way with the help of open/closed fittings. With the feeding of water the retentate is diluted, so that the viscosity decreases and the unit can then be started up again normally.

For the retentate feeding to the module or module group, i.e. several modules connected in series, it is known to supply the individual module groups or the individual modules asymmetrically for the purpose of running the pipeline in a simple way. For this purpose several side pipelines branch off from the main line one after another to the individual module groups or to the individual modules. The same is also true for the retentate discharge from the module groups. Another, known design uses three modules, which are supplied symmetrically in three individual pipelines by a branching of the main line.

The addition of water as a flushing agent to the retentate cycle and the known method of conveying the retentate to the module group, in particular the symmetrical inflow and discharge, can contribute in simple cases to lessening the danger of the clogging of the modules. If however, as in the present case, the unit is being run with a very high proportion of solids in the retentate cycle, these known measures, in the above emergency situations, no longer suffice to flush out the filtration modules with water.

SUMMARY OF THE INVENTION

The object of the invention is thus to create a process or a safety arrangement for the initially mentioned unit that guarantees a smooth operation by eliminating the danger of clogging in the filtration modules, in particular when there is a very high proportion of solids in the retentate cycle.

According to the invention, this object is attained in that the retentate side of the cross flow filtration modules, when the unit is shut down, is charged with the addition of flushing agent that increases over time and/or is geometrically fractionated.

BRIEF DESCRIPTION OF THE DRAWING FIGURE

The invention is explained in greater detail in the following description and the drawing which shows an embodiment in diagrammatic representation.

DETAILED DESCRIPTION OF THE INVENTION

The raw juice to be clarified is fed by pipe 1 to retentate circulation cycle 2 of cross flow filtration device 3, which preferably consists of a microfiltration or an ultrafiltration device. The unit can be operated continuously in single-stage or multistage. However, the process according to the invention can also be used for a semi-continuous cross flow filtration operated in batch process. For this purpose pipe 1 is connected to buffer tank 4, into which the retentate is carried back by pipe 5 (in the drawing represented with dotted lines as an alternative). In retentate circulation cycle 2 of cross flow filtration device 3, single-stage and continuous in the embodiment, are placed circulating pump 6, stage inlet valve 7 and stage outlet valve 8. The permeate of cross flow filtration device 3 is carried off by pipe 9. To improve the filtration yield the unit is run with a very high proportion of solids in retentate circulation cycle 2. The danger of clogging of filtration module 10 of cross flow filtration device 3 that thus arises, in particular when the unit is shut down by a power failure for example, is met by the delivery of flushing agents, preferably water. For this purpose pipe 11 is provided, that discharges on the retentate side of cross flow filtration device 3 into retentate circulating cycle 2 after circulating pump 6 and stage inlet valve 7.

To achieve the best possible flushing action, the flushing agent is introduced with a dosage or at a flow rate that increases over time and/or is geometrically fractionated into retentate circulation cycle 2. In this way the delivery of flushing agent can take place continuously or in steps. An addition of flushing agent purely increasing over time can be achieved, for example, by beginning with a small quantity of flushing agent and increasing this over time, preferably slowly, instead of flushing right from the beginning with a specific constant quantity of flushing agent. The addition of the flushing agent can also begin with a relatively viscous flushing agent, having a viscosity somewhat less than the retentate, and then the viscosity of the flushing agent is decreased over time. This can take place, for example, through the metered addition of water to the flushing agent.

A purely geometrically increasing supply of flushing agent can take place, for example, by a fractionated supply of the flushing agent at various places of retentate circulation cycle 3, and the overall quantity can be constant over time. The fractionated supply is achieved in the embodiment by the branching of pipe 11 into several individual pipes 12, which discharge one after another into retentate circulation cycle 3 after stage inlet valve 7.

The duration of the supply of flushing agent, to start with small, until the full supply of flushing agent, should be at least 30 seconds. The full supply of flushing agent is normally determined in that after the addition of water the normal pipe pressure at the place of supply prevails in the retentate pipe.

Because of the above relatively mild measures it is achieved that the more viscous retentate mixes with the flushing agent, so that it becomes possible to flush out the retentate in filtration modules 10. This does not result in the channeling of a flushing agent of relatively low viscosity (water) through the viscous retentate, which prevents a complete flushing.

The supply of flushing agent can take place in principle at any place in retentate circulating cycle 2, however preferably downstream after circulating pump 6, so that a sufficient margin of safety is provided, in the event circulation pump 6 is no longer running because of a power failure.

Water is normally used as flushing agent. In exceptional cases, however, even more viscous flushing agents can be used, for example retentate, preferably sulfurated, from previous filtration cycles or discharge from continuous filtration. In noncritical cases, a suspension manufactured for this purpose from different kinds of materials is also possible.

Filtration modules 10 of cross flow filtration device 3 are preferably designed with wide conduits with a conduit diameter or a conduit width of at least 4 mm. Preferably pipe modules are used, because in this way a particularly uniform flow is achieved and no corners with no-flow places are present.

In the embodiment eight individual filtration modules or eight module presses or eight module presses with several individual modules connected in series are provided. The supply of retentate to filtration modules 10 takes place symmetrically by pipe 13, which branches into two pipes, from which in turn each pipe branches into two further pipes, so that filtration modules 10 are supplied symmetrically and centrally in the order of priority. The same pipe branching takes place on the discharge side of filtration modules 10 by joining the retentate discharge pipes into one pipe 14 that is located in retentate circulation cycle 2.

In further embodiments each unit stage of cross flow filtration device 3 can consist preferably of two, four, eight, sixteen etc. module groups or individual modules. The feeding or the discharging can take place centrally in order of priority in groups of two, four, eight, sixteen etc. module groups or individual modules.

By the above mentioned placement and supplying of filtration modules 10 a uniform flushing of all filtration modules is assured. Thus it is avoided that, e.g., individual filtration modules are not as well flushed and thus the danger of clogging is increased.

Preferably cross flow filtration device 3 is supplied with flushing agent by pipe 15 from storage tank 16 which contains, e.g., softened water or condenser water and which is connected to a source of compressed air by a pipe 17. In this way the flushing agent is very quickly available in emergencies.

To automate the gradually increasing delivery of flushing agent over time the quantity added and/or the decrease in the viscosity of the flushing agent is controlled or regulated. The control can take place according to a time schedule in stages or steps, or constantly changing. The regulation can be carried out as a function of one of the process variables affected by the flushing. Both measures for controlling and regulating can also be used in combination. In the embodiment the quantity of flow-through of the retentate after filtration modules 10 can be measured by measuring position 18 placed in retentate circulation cycle 2 and transmitted by control pipe 19 to control/regulating organ or device 20. Regulating valve 21 located in flushing agent supply pipe 11 is controlled from there.

Independently from these control or regulating processes, in the case of a power failure, for example, stage inlet valve 7 is automatically closed and stage outlet valve 8 is completely opened.

Because of these measures it is also possible to allow a cross flow filtration unit being operated with a very high cloudiness proportion in the retentate cycle to shut down by push button or by automatic control from outside, without there being any danger of clogging for the filtration modules. Besides easier operation, as a result additional possibilities for automation arise in connection with the automation of whole production pipes.

The use of the present invention is not limited to the examples described. It can also be used to advantage, if for economic reasons, given by the product losses, as high yields as possible are to be achieved (expensive products).

A further use is possible, if for economic reasons, dictated by the overall process costs, for example when there is subsequent drying or storage, a product that is as dry as possible is to be achieved, as is the case in sewage engineering, for example.

Furthermore the use of the invention is not limited to the module system described. Rather it can basically be used to advantage for all known module systems.

What is claimed is:

1. Process for flushing filtration modules of a unit for clarifying a liquid by cross flow filtration which is run with a proportion of solids in a retentate circulation circuit, comprising feeding to a retentate side of the filtration modules a supply of flushing agent at a flow rate that increases over time to help prevent clogging of the filtration modules if the unit shuts downs, the flushing being in the form of a liquid having a viscosity less than the viscosity of the retentate.

2. Process according to claim 1, wherein the increase in flow rate over time of the supply of flushing agent takes place continuously.

3. Process according to claim 1, wherein the duration of the supply of flushing agent is at least 30 seconds.

4. Process according to claim 3, wherein the viscosity of the flushing agent is lessened by measured addition of water.

5. Process according to one of claim 1, wherein the flushing agent is added at several places of the retentate circulation circuit and the total amount of flushing agent is constant over time.

6. Process according to claim 1, wherein the retentate circulation circuit includes a circulation pump, and the supply of flushing agent takes place downstream from the circulation pump.

7. Process according to claim 1, wherein the flushing agent has a higher viscosity than water.

8. Process according to claim 7, wherein the flushing agent includes a filtered retentate.

9. Process according to claim 7, wherein the flushing agent includes a suspension of materials that is different from the liquid being clarified.

10. Process according to claim 1, wherein the filtration modules have conduits possessing a conduit diameter or a conduit width of at least 4 mm.

11. Process according to claim 10, wherein said filtration modules are pipe modules.

12. Process according to claim 1, wherein the flushing agent is taken from a storage tank containing softened water or condenser water.

13. Process according to claim 1, wherein the increase in flow rate over time of the flushing agent is controlled with a control device.

14. Process according to claim 13, wherein the increase in flow rate over time of the flushing agent is controlled so as to take place in steps by a time schedule or in a continuously changing manner.

15. Process according to claim 13, wherein the quantity of the flushing agent is controlled based on an amount of flow-through in the retentate circulation circuit at a point downstream of the cross flow filtration modules.

16. Process according to claim 1, including a retentate supply pipe connected to each filtration module, each retentate supply pipe being connected to a common supply pipe.

17. Process according to claim 1, including a retentate discharge pipe connected to each filtration module, said discharge pipes being connected to one pipe.

18. Process according to claim 1, wherein the filtration modules comprise at least two module groups or individual modules.

19. Process according to claim 1, wherein the flushing agent is centrally supplied to the filtration modules which are arranged in groups of at least two modules.

20. Process according to claim 1, wherein the filtration modules are arranged in groups of at least two modules, and an outflow from the filtration modules takes place centrally.

21. Process according to claim 1, wherein the increase in flow rate over time of the supply of flushing agent takes place in steps.

* * * * *

UNITED STATES PATENT AND TRADEMARK OFFICE
CERTIFICATE OF CORRECTION

PATENT NO. : 6,113,791
DATED : September 5, 2000
INVENTOR(S) : Eduard HARTMANN

It is certified that error appears in the above-indentified patent and that said Letters Patent is hereby corrected as shown below:

Column 4, line 46, claim 1, after "flushing" insert --agent--.

Column 4, line 56, claim 5, delete "one of".

Signed and Sealed this

Fifteenth Day of May, 2001

Attest:

NICHOLAS P. GODICI

Attesting Officer      Acting Director of the United States Patent and Trademark Office